(12) United States Patent
Chen et al.

(10) Patent No.: US 9,861,363 B2
(45) Date of Patent: Jan. 9, 2018

(54) LINEAR SURGICAL STAPLER

(71) Applicant: TOUCHSTONE INTERNATIONAL MEDICAL SCIENCE CO., LTD., Suzhou, Jiangsu Province (CN)

(72) Inventors: Wangdong Chen, Suzhou (CN); Tuo Shu, Suzhou (CN); Kaifen Fu, Suzhou (CN)

(73) Assignee: TOUCHSTONE INTERNATIONAL MEDICAL SCIENCE CO., LTD., Suzhou, Jiangsu Province (CN)

( * ) Notice: Subject to any disclaimer, the term of this patent is extended or adjusted under 35 U.S.C. 154(b) by 383 days.

(21) Appl. No.: 14/428,366

(22) PCT Filed: Sep. 10, 2013

(86) PCT No.: PCT/CN2013/083175
§ 371 (c)(1),
(2) Date: Mar. 14, 2015

(87) PCT Pub. No.: WO2014/040520
PCT Pub. Date: Mar. 20, 2014

(65) Prior Publication Data
US 2015/0265275 A1 Sep. 24, 2015

(30) Foreign Application Priority Data
Sep. 14, 2012 (CN) .......................... 2012 1 0338314

(51) Int. Cl.
*A61B 17/072* (2006.01)
*A61B 90/00* (2016.01)

(52) U.S. Cl.
CPC .................. *A61B 17/07207* (2013.01); *A61B 2017/07285* (2013.01); *A61B 2090/034* (2016.02); *A61B 2090/0801* (2016.02)

(58) Field of Classification Search
CPC .... A61B 17/07207; A61B 2017/07285; A61B 2090/0814
See application file for complete search history.

(56) References Cited

U.S. PATENT DOCUMENTS 5,129,570 A * 7/1992 Schulze ........... A61B 17/07207
227/175.2
9,433,414 B2 * 9/2016 Chen ................ A61B 17/07207
(Continued)

FOREIGN PATENT DOCUMENTS

| CN | 201719300 U | 1/2011 |
| CN | 101991450 A | 3/2011 |

(Continued)

*Primary Examiner* — Andrew M Tecco
(74) *Attorney, Agent, or Firm* — Cheng-Ju Chiang

(57) ABSTRACT

A linear surgical stapler includes upper and lower jaws, a staple cartridge arranged at a distal end of the lower jaw, a firing piece movably arranged relative to the staple cartridge, and a cutter advancer having a cutter. The firing piece and the cutter advancer are kept relatively still. The linear surgical stapler also includes a lower safety block having a raised stopper. When the linear surgical stapler is in an initial state without loading the staple cartridge, at least a part of the raised stopper is arranged on the movement path of the firing piece. The safety mechanism of the linear surgical stapler is structurally simple, convenient to process, also safe and reliable.

8 Claims, 6 Drawing Sheets

(56) References Cited

U.S. PATENT DOCUMENTS

| | | | |
|---|---|---|---|
| 2011/0180586 A1 | 7/2011 | Shah | |
| 2013/0264370 A1* | 10/2013 | Chen | A61B 17/07207 227/175.2 |
| 2013/0264372 A1* | 10/2013 | Chen | A61B 17/07207 227/177.1 |

FOREIGN PATENT DOCUMENTS

| | | | |
|---|---|---|---|
| CN | 102068290 A | 5/2011 | |
| CN | 202409017 U | 9/2012 | |
| WO | WO 2012079455 A1 * | 6/2012 | A61B 17/07207 |

* cited by examiner

LINEAR SURGICAL STAPLER

CROSS REFERENCE TO RELATED APPLICATIONS

The present application is a 35 U.S.C. §371 National Phase conversion of International (PCT) Patent Application No. PCT/CN2013/083175, filed on Sep. 10, 2013, the disclosure of which is incorporated by reference herein. The PCT International Patent Application was filed and published in Chinese, and claims the benefit of priority to Chinese Patent Application No. 201210338314.3 titled "LINEAR SURGICAL STAPLER", filed with the Chinese State Intellectual Property Office on Sep. 14, 2012, the entire disclosure of which is incorporated herein by reference.

TECHNICAL FIELD

The present application relates to a medical stapling instrument, and more particularly to a linear surgical stapler, which belongs to the technical field of medical instruments.

BACKGROUND

Linear surgical staplers are widely used in surgical operations for wound closure, and internal tissue closure and excision. A typical linear surgical stapler as disclosed in U.S. Pat. No. 5,129,570 performs two functions of stapling and cutting, to remove the redundant tissue while stapling the wound. This kind of linear surgical stapler generally includes two jaws (i.e., an upper jaw and a lower jaw), a closing handle for closing the upper jaw and the lower jaw, a staple anvil and a staple cartridge arranged opposite to each other at distal ends of the upper jaw and lower jaw respectively, a firing piece and a cutter advancer with a cutter at the distal end which are arranged in the staple cartridge and are moveable synchronously relative to the staple cartridge, and an operation button for driving movement of the firing piece and the cutter advancer. Staples are arranged in the staple cartridge. The firing piece pushes a staple driver successively and pushes the staples towards the staple anvil. The cutter cuts off the tissue between the staple cartridge and the staple anvil.

In the prior art, the staple cartridge of the instrument can be used for multiple times by being replaced. In clinical application, multiple times of stapling and cutting tissues are often required, and thus the staple cartridge is required to be replaced for many times in an operation. When no staple cartridge is loaded, the operation button can be pushed forwards arbitrarily, and then the cutter may be pushed forwardly. This may cause serious consequence as arising from only cutting without stapling.

SUMMARY

An object of the present application is to provide a linear surgical stapler having a safety mechanism with simple structure.

The object of the present application will be implemented by the following technical solutions.

A linear surgical stapler includes:
upper and lower jaws, the lower jaw including a staple cartridge located at a distal end thereof;
a firing piece movable relative to the staple cartridge, and a cutter advancer including a cutter located at a distal end thereof; and
a lower safety block including a raised stopper, when the linear surgical stapler is under an initial status with the staple cartridge unloaded in the lower jaw, at least part of the raised stopper is blockaded in a movement path of the firing piece.

Further, the raised stopper always suffers a force towards the upper jaw.

Still further, the staple cartridge includes a protrusion formed on a bottom surface thereof. The protrusion is capable of pressing against and pushing away the raised stopper in the movement path of the firing piece.

Still further, the firing piece includes a connecting piece. The lower jaw includes an opening for mating with the raised stopper. When the linear surgical stapler is under the initial status, at least part of the raised stopper extends through the opening to abut against a distal face of the connecting piece.

Still further, the lower safety block includes a body. The body and the raised stopper are connected with each other by a flexible beam. The body keeps stationary with respect to the lower jaw.

Still further, linear surgical stapler further includes an upper safety block to connect with the lower safety block.

Still further, the lower safety block includes a body with a hook. The upper safety block is lockable with the hook to keep stationary with respect to the body.

Still further, the upper safety block defines a passageway through which the cutter advancer extends.

Still further, the cutter advancer includes a step. When the cutter advancer resets back to the initial status of the linear surgical stapler, the step abuts against a distal surface of the passageway of the upper safety block.

Still further, the lower jaw is U-shaped and includes therein the firing piece and the cutter advancer. The proximal ends of the firing piece and the cutter advancer are associated with a single slider for driving movement thereof.

The present application has main beneficial effects such as a simple structure, easy to be manufactured, safe and reliable, as well as good promotion value.

ILLUSTRATED EMBODIMENTS

Figure 1:
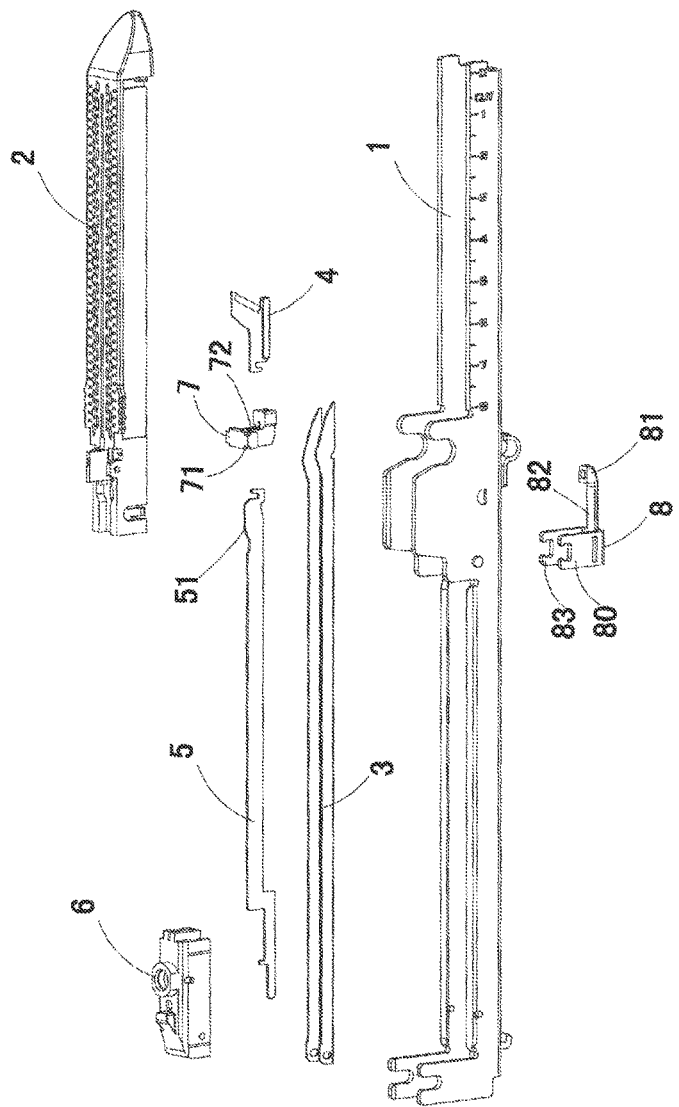
FIG. 1 is a schematic exploded view of a lower jaw in accordance with an illustrated embodiment of the present application.

Referring to FIG. 1, the present application provides a linear surgical stapler having a safety mechanism. In accordance with the prior art, the linear surgical stapler includes a plastic housing, and upper and lower jaws capable of being mutually closed or opened relative to each other. The upper jaw includes a staple anvil (not shown) installed at a distal end thereof. The lower jaw 1 includes a staple cartridge 2 installed at the distal end thereof. The position defined in the present application is trying for clear expression. Of course, the position of the upper jaw and the lower jaw 1 are interchangeable.

The lower jaw 1 is U-shaped and includes therein a firing piece 3 and a cutter advancer 5 which includes a cutter 4 at the distal end thereof. The firing piece 3 and the cutter advancer 5 are movable relative to the staple cartridge 2. The proximal ends of the firing piece 3 and the cutter advancer 5 are associated with a single slider 6 for driving movement thereof. In use, the tissue is placed between the staple anvil and the staple cartridge; then, the upper and lower jaws are moved towards each other and the handle is closed so as to enable the upper and lower jaws to clamp the tissue; and then, the firing push button arranged at proximal ends of the upper and lower jaws is pushed. As a result, the slider 6 connected with the firing push button drives movement of the firing piece 3 and the cutter advancer 5 to staple and cut the tissue. It is understandable that when the firing piece 3 can not be movably pushed, the cutter 4 can not cut the tissue as well.

The present application is characterized in that the linear surgical stapler is provided with the safety mechanism between the firing piece 3 and the lower jaw 1. The safety mechanism includes an upper safety block 7 and a lower safety block 8. Both the upper safety block 7 and the lower safety block 8 are fixed to the lower jaw 1. The lower safety block 8 includes a raised stopper 81 and the lower jaw includes an opening 11 for mating with the raised stopper 81. When the linear surgical stapler is under an initial status with the staple cartridge 2 unloaded in the lower jaw 1, at least part of the raised stopper 81 is mounted in the movement path of the firing piece 3. The raised stopper 81 always suffers a force towards the upper jaw.

Figure 2:
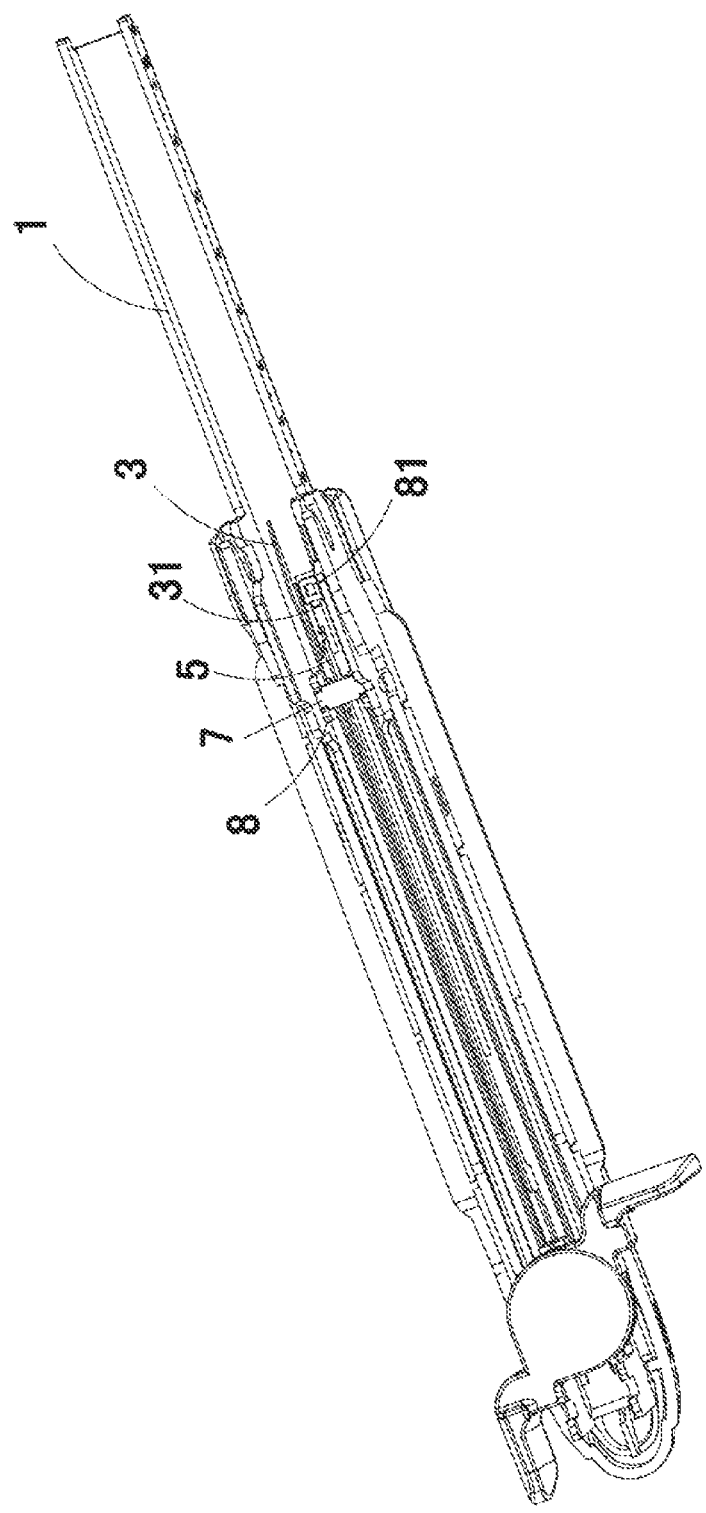
FIG. 2 is a schematic structural view of the lower jaw with a staple cartridge being not shown.
Figure 3:
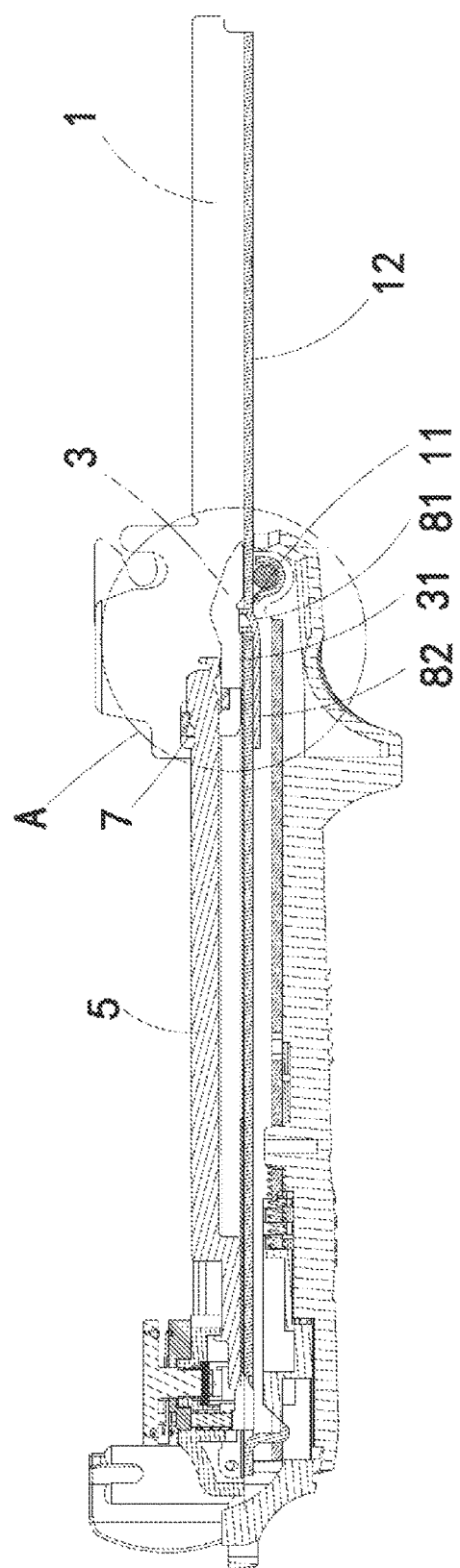
FIG. 3 is a schematic cross-sectional view of the lower jaw with the staple cartridge being not shown.
Figure 3A:
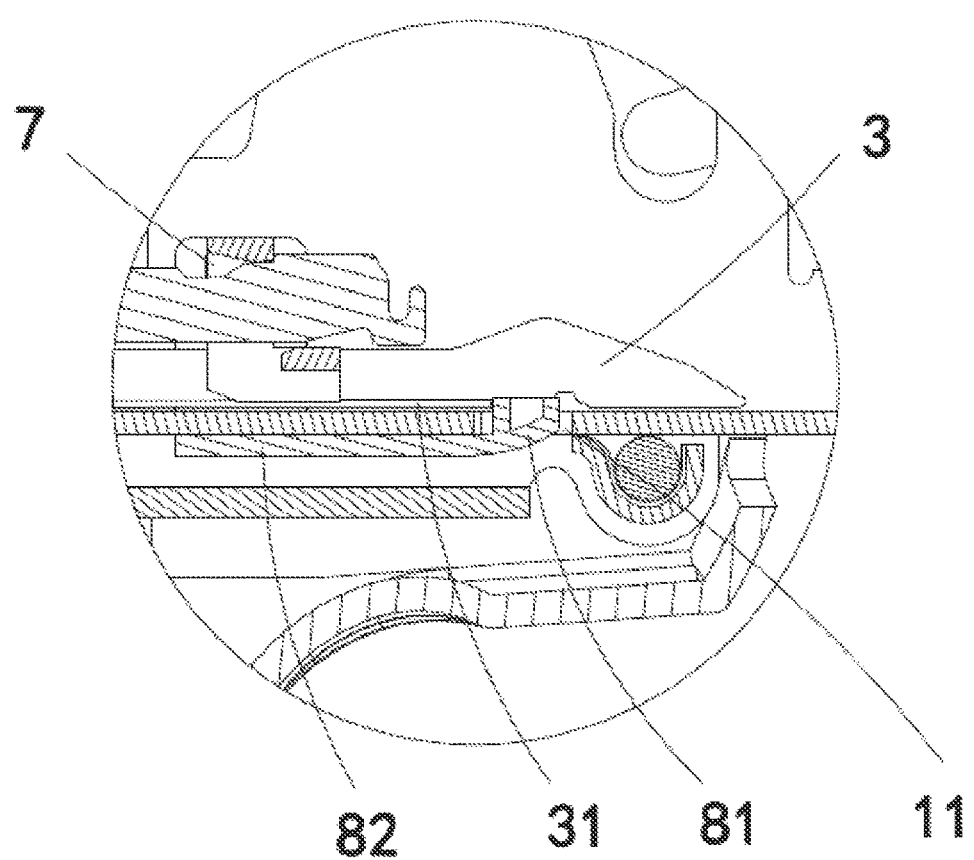
FIG. 3a is an enlarged view of the circle A as shown in FIG. 3.

Referring to FIGS. 2, 3 and 3a, the firing piece 3 includes a connecting piece 31. When the linear surgical stapler is under the initial status before the staple cartridge 2 is loaded in the lower jaw 1, the raised stopper 81 extends through the opening 11 to abut against a distal face of the connecting piece 31. As a result, when the linear surgical stapler is under the initial status before the staple cartridge 2 is loaded in the lower jaw 1, the movement of the firing piece 3 is restricted by the raised stopper 81 for safety purpose.

In detail, the lower safety block 8 includes a body 80. The raised stopper 81 is relatively opposite to the body 80. The body 80 and the raised stopper 81 are connected with each other by a flexible beam 82. The flexible beam 82 makes the raised stopper 81 always suffering a force towards the upper jaw. The body 80 of the lower safety block 8 includes a hook 83 and the upper safety block 7 includes a recess 71 for mating with the hook 83. The lower jaw 1 further includes a slot from which the body 80 of the lower safety block 8 extends. The slot is located nearer to the proximal end of the lower jaw 1 than that of the opening 11. The lower safety block 8 is designed to be lockable with the lower jaw 1. The body 80 of the lower safety block 8 is capable of keeping stationary with respect to the lower jaw 1 through a locking mechanism. In assembling the safety mechanism, firstly the lower safety block 8 is mounted to the lower jaw 1 through the slot and the opening 11 to make the hook 83 extending into the lower jaw 1; and then, the upper safety block 7 is mounted to lock with the hook 83 of the lower safety block 8. As a result, the upper safety block 7 is capable of keeping stationary with respect to the body 80 of the lower safety block 8. When the upper safety block 7 and the lower safety block 8 are fixed together, the flexible beam 82 of the lower safety block 8 closely presses against a bottom surface 12 of the lower jaw 1.

Figure 4:
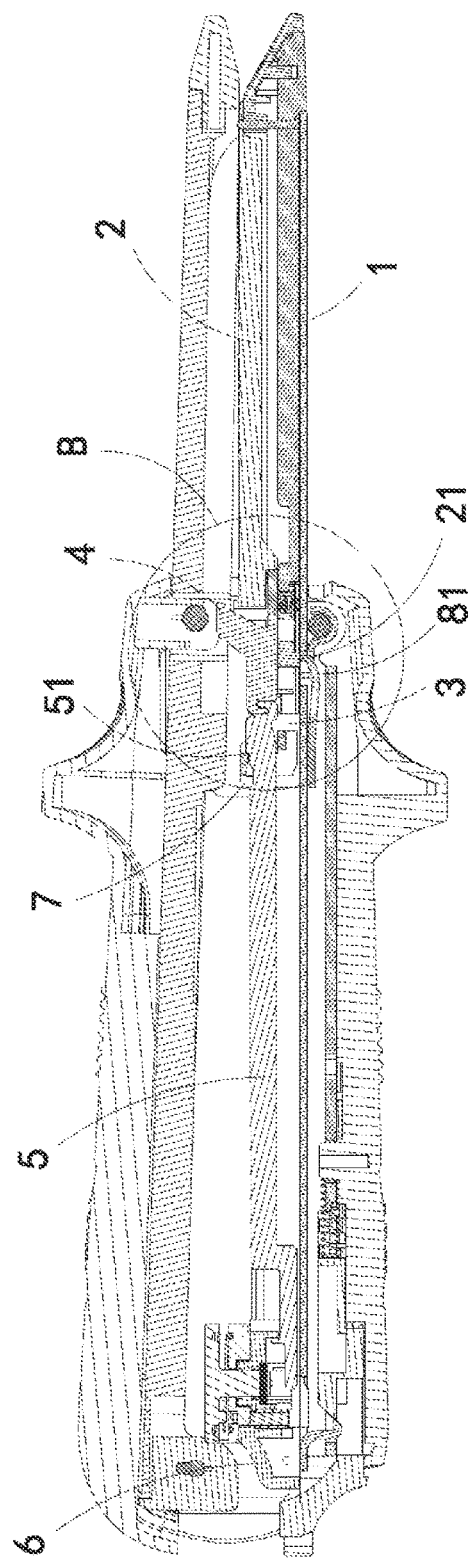
FIG. 4 is a schematic cross-sectional view of the lower jaw with the staple cartridge mounted therein.
Figure 4A:
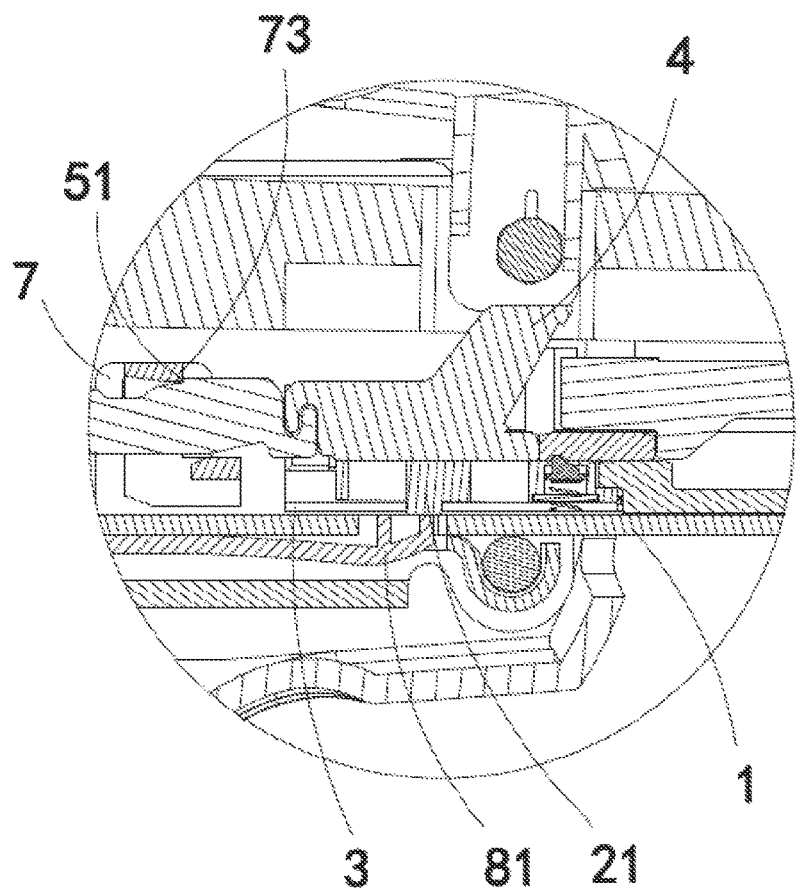
FIG. 4a is an enlarged view of the circle B as shown in FIG. 4.

Referring to FIGS. 4 and 4a, the staple cartridge 2 includes a protrusion 21 formed on a bottom surface thereof. The protrusion 21 is capable of pressing against and pushing away the raised stopper 81 in the movement path of the firing piece 3. Under this condition, the safety mechanism is released and the linear surgical stapler can be freely used for cutting and stapling.

Figure 5:
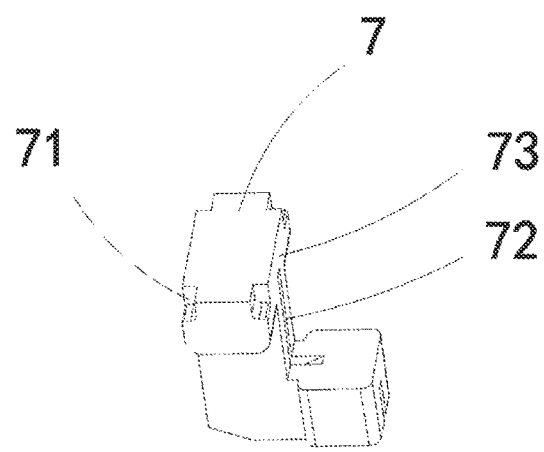
FIG. 5 is a schematic structural view of an upper safety block of the present application.

Referring to FIG. 5, the upper safety block 7 includes a passageway 72 along which the cutter advancer 5 moves. The cutter advancer 5 includes a step 51. When the cutter advancer 5 resets back to the initial status of the linear surgical stapler, the step 51 is capable of abutting against a distal surface 73 of the upper safety block 7 for easily replacing a new staple cartridge and mating with the cutter 4 and the cutter advancer 5.

In the present application, the proximal end refers to the end close to the user, on the contrary, the distal end refers to the end far from the user. The present application still includes a variety of embodiments. All the technical solutions formed by the equivalent variation or the equivalent modification fall into the protection scope of the present application.

What is claimed is:

1. A linear surgical stapler comprising:
    upper and lower jaws, the lower jaw comprising a staple cartridge located at a distal end thereof;
    a firing piece movable relative to the staple cartridge, and a cutter advancer comprising a cutter located at a distal end thereof;
    a lower safety block comprising a raised stopper, when the linear surgical stapler is under an initial status with the staple cartridge unloaded in the lower jaw, at least part of the raised stopper is blockaded in a movement path of the firing piece; and
    an upper safety block to connect with the lower safety block, wherein the lower safety block comprises a body which comprises a hook, the upper safety block is lockable with the hook to keep stationary with respect to the body.

2. The linear surgical stapler as claimed in claim 1, wherein the raised stopper always suffers a force towards the upper jaw.

3. The linear surgical stapler as claimed in claim 2, wherein the lower safety block comprises a body, the body and the raised stopper are connected with each other by a flexible beam, and the body keeps stationary with respect to the lower jaw.

4. The linear surgical stapler as claimed in claim 1, wherein the staple cartridge comprises a protrusion formed on a bottom surface thereof, the protrusion being capable of pressing against and pushing away the raised stopper in the movement path of the firing piece.

5. The linear surgical stapler as claimed in claim 1, wherein the firing piece comprises a connecting piece, the lower jaw comprises an opening for mating with the raised stopper, when the linear surgical stapler is under the initial status, the at least part of the raised stopper extends through the opening to abut against a distal face of the connecting piece.

6. The linear surgical stapler as claimed in claim 1, wherein the upper safety block defines a passageway through which the cutter advancer extends.

7. The linear surgical stapler as claimed in claim 6, wherein the cutter advancer comprises a step, when the cutter advancer resets back to the initial status of the linear surgical stapler, the step abuts against a distal surface of the passageway of the upper safety block.

8. The linear surgical stapler as claimed in claim 1, wherein the lower jaw is U-shaped and comprises therein the firing piece and the cutter advancer, the proximal ends of the firing piece and the cutter advancer are associated with a single slider for driving movement thereof.

* * * * *